(12) United States Patent
Lamoureux et al.

(10) Patent No.: US 11,944,844 B2
(45) Date of Patent: Apr. 2, 2024

(54) INTERNAL BODY CAVITY THERAPEUTIC APPLICATORS AND METHODS FOR USING THEM

(71) Applicants: Gary Lamoureux, Woodbury, CT (US); Juan-Carlos Diaz, Pembroke, FL (US); Gil'ad Cohen, Tenafly, NJ (US)

(72) Inventors: Gary Lamoureux, Woodbury, CT (US); Juan-Carlos Diaz, Pembroke, FL (US); Gil'ad Cohen, Tenafly, NJ (US)

( * ) Notice: Subject to any disclaimer, the term of this patent is extended or adjusted under 35 U.S.C. 154(b) by 0 days.

(21) Appl. No.: 17/823,248

(22) Filed: Aug. 30, 2022

(65) Prior Publication Data

US 2022/0409926 A1 Dec. 29, 2022

Related U.S. Application Data

(63) Continuation of application No. 15/300,674, filed as application No. PCT/US2015/023569 on Mar. 31, 2015, now Pat. No. 11,446,515.

(60) Provisional application No. 61/974,307, filed on Apr. 2, 2014.

(51) Int. Cl.
  *A61N 5/10* (2006.01)
(52) U.S. Cl.
  CPC ............. *A61N 5/10* (2013.01); *A61N 5/1002* (2013.01); *A61N 5/1007* (2013.01); *A61N 5/1014* (2013.01); *A61N 2005/1003* (2013.01)
(58) Field of Classification Search
  CPC .......... A61N 5/10002; A61N 5/10003; A61M 25/1011; A61M 2025/1047; A61M 2025/1061
  See application file for complete search history.

(56) References Cited

U.S. PATENT DOCUMENTS

| 4,951,686 | A | * | 8/1990 | Herlitze | A61M 25/09 |
| | | | | | 604/528 |
| 5,540,659 | A | * | 7/1996 | Teirstein | A61N 5/1002 |
| | | | | | 600/3 |
| 6,149,575 | A | * | 11/2000 | Leonhardt | A61M 25/1011 |
| | | | | | 604/101.02 |
| 6,527,692 | B1 | * | 3/2003 | Weinberger | A61N 5/1002 |
| | | | | | 600/3 |
| 2005/0124843 | A1 | * | 6/2005 | Singh | A61N 5/1014 |
| | | | | | 600/3 |
| 2006/0224114 | A1 | * | 10/2006 | van Sloten | A61M 25/0009 |
| | | | | | 604/103.1 |
| 2009/0054922 | A1 | * | 2/2009 | Broker | A61M 25/1011 |
| | | | | | 604/509 |
| 2010/0185173 | A1 | * | 7/2010 | Popowski | A61N 5/1007 |
| | | | | | 604/99.01 |
| 2012/0078029 | A1 | * | 3/2012 | Subramanian | A61M 25/1011 |
| | | | | | 600/3 |

* cited by examiner

*Primary Examiner* — Samuel G Gilbert (74) *Attorney, Agent, or Firm* — Handal & Morofsky LLC; Anthony H. Handal (57) ABSTRACT

An apparatus for providing treatment to at least one tissue includes a distal balloon, a proximal balloon, and an intermediate balloon positioned between the distal balloon and the proximal balloon and inflatable independently from the distal and proximal balloons. A source lumen is positioned within at least the intermediate balloon receives a radiation source to treat target tissue adjacent the intermediate balloon.

20 Claims, 8 Drawing Sheets

INTERNAL BODY CAVITY THERAPEUTIC APPLICATORS AND METHODS FOR USING THEM

TECHNICAL FIELD

The present disclosure relates to apparatus and methods for treating internal tissue disorders, and more particularly, to apparatus and methods for the treatment of such disorders by direct application of radiation therapy to areas within a patient's body.

BACKGROUND

Internal tissue disorders (e.g., cancer) can be a result of genetic-malformations or can arise from sickness or trauma. Such disorders can typically be treated, for example, with, the application of pharmaceuticals (e.g., directly or systemically), by the application of tissue altering forces (e.g., radiotherapy), or by surgical intervention.

Where radiotherapy is the chosen treatment, it would be advantageous, to the extent possible, to limit exposure of collateral healthy tissue to the treatment and maximize radiotherapy treatment of the internal tissue disorder.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

An apparatus for providing treatment to at least one tissue includes a distal balloon, a proximal balloon, and at least one intermediate balloon positioned between the distal balloon and the proximal balloon and inflatable independently from the distal and proximal balloons. A source lumen positioned within at least the intermediate balloon receives a radiation source to treat target tissue adjacent the intermediate balloon.

By providing independently inflatable balloons, applicators in accordance with the present disclosure allow a radiation dose to be maximally applied to the internal tissue disorder, and yet minimally applied to the surrounding area, thus limiting the patient's adjacent healthy tissue to unnecessary exposure to the radiation, as well as any possible side effects.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

Further scope of applicability of the present disclosure will become apparent from the detailed description given hereinafter. However, it should be understood that the detailed description and specific examples, while indicating specific embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The above and other aspects, features, and advantages of the present disclosure will become more apparent in light of the following detailed description when taken in conjunction with the accompanying drawings in which.

The figures depict specific embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Particular embodiments of the present disclosure are described hereinbelow with reference to the accompanying drawings; however, it is to be understood that the disclosed embodiments are merely exemplary and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Like reference numerals may refer to similar or identical elements throughout the description of the figures. As shown in the drawings and described throughout the following description, as is traditional when referring to relative positioning on a surgical instrument, the term "proximal" refers to the end of the apparatus which is closer to the user and the term "distal" refers to the end of the apparatus which is farther away from the user. The term "clinician" refers to any medical professional (i.e., doctor, surgeon, nurse, or the like) performing a medical procedure involving the use of embodiments described herein.

The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

The exemplary embodiments of the present disclosure relate to an applicator that can be used to treat internal tissue disorders by targeting radiotherapy treatments directly to the internal tissue disorder. For example, the exemplary applicator can use a plurality of balloons, only some of which are inflated, to provide the treatment directly to the disorder depending on where adjacent the tubular structure the disorder is located. Those having ordinary skill in the art will understand that the exemplary embodiments of the present disclosure can be implemented in any tubular structure in the body of a patient (e.g., the rectum, the nose, the lungs, the GI track, vascular system, the esophagus, etc).

Figure 1:
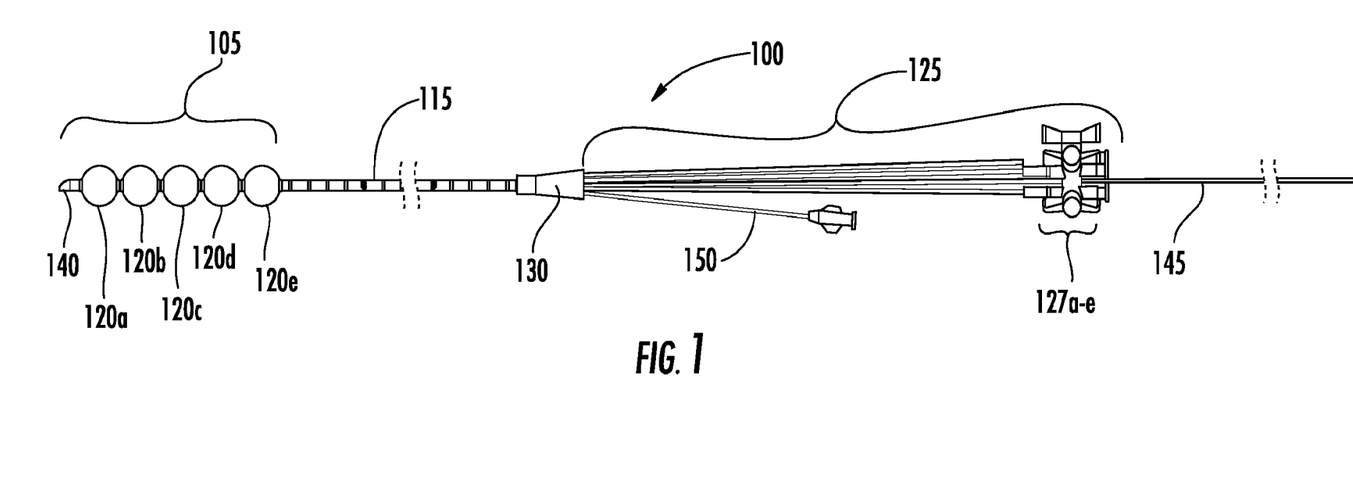
FIG. 1 is a side view of an exemplary applicator according to an exemplary embodiment of the present disclosure.

FIG. 1 shows a side view of an exemplary applicator/arrangement apparatus 100 according to an exemplary embodiment of the present disclosure in an inflated form, for delivering treatment to an internal tissue disorder. Exemplary applicator 100 has a distal or treatment portion 105 configured to be inserted into the tubular structure, a flexible elongated shaft 115, a proximal portion 125 (e.g., inflation lumens, source lumen and guide wire lumen), and a hub 130 positioned between the proximal end of flexible elongated shaft 115 and proximal portion 125. A source lumen 145 extends from proximal portion 125 through the center of applicator 100 to distal portion 105. In embodiments, a guide lumen 150 also extends from proximal portion 125 through the center of applicator 100 to distal portion 105.

Distal portion 105 can include a separate tip 140 which can be configured to aid in the insertion of applicator 100 into the tubular structure and track on the guide wire. For example, tip 140 can taper distally to a width smaller than the width of distal portion 105, and can increase in size proximally. Distal tip 140 may also include a marker 142 (FIG. 2) that is visible to an imaging system (not shown) to confirm accurate placement of the applicator 100 relative to tissue to be treated. In embodiments, marker 142 is a radiopaque marker. Optionally, a lubricant (e.g., liquid, gel or the like), is used to aid insertion into a tubular structure by inserting tip 140 into the tubular structure.

Figure 2:
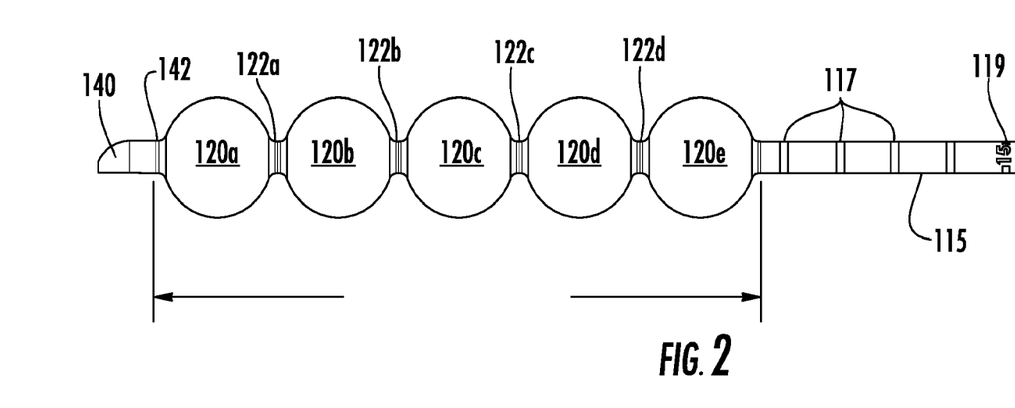
FIG. 2 is an enlarged side view of the distal or treatment end of the exemplary applicator according to FIG. 1.
Figures 3, 4:
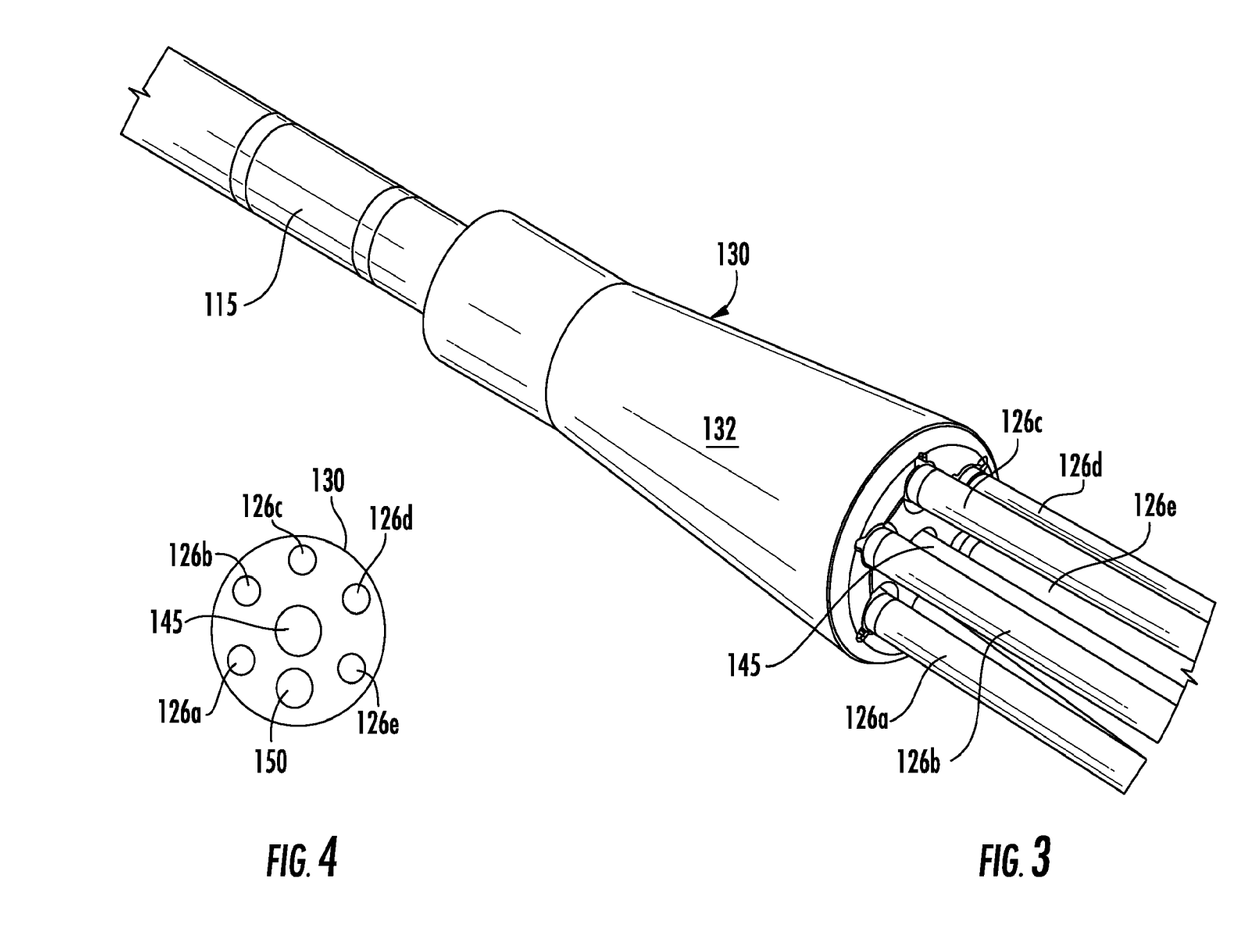
FIG. 3 is perspective view of a hub of the exemplary applicator according to FIG. 1.
FIG. 4 is cross-sectional view through the flexible elongated shaft of the exemplary applicator according to FIG. 1.
Figure 5A:
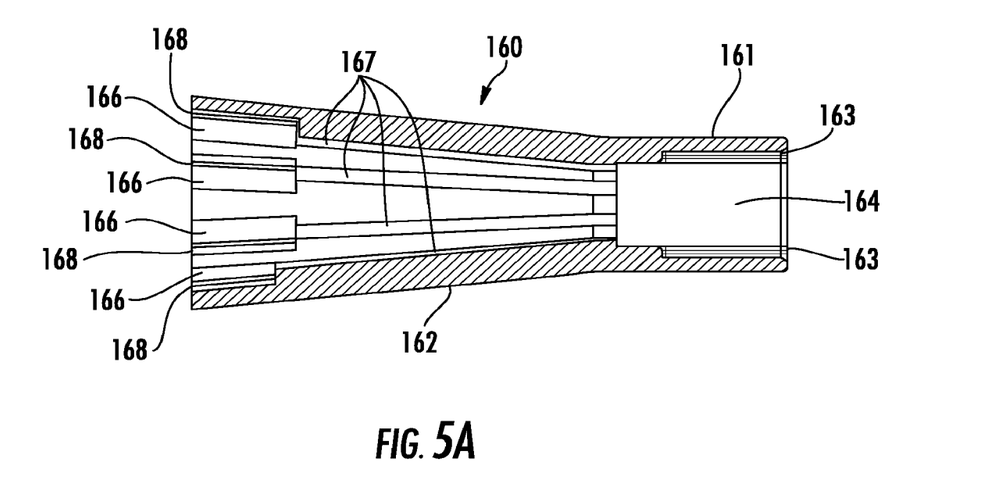
FIGS. 5A and 5B are cross sectional views of the outer body of the hub and the hub insert, respectively, of the exemplary applicator according to FIG. 1.
Figure 5B:
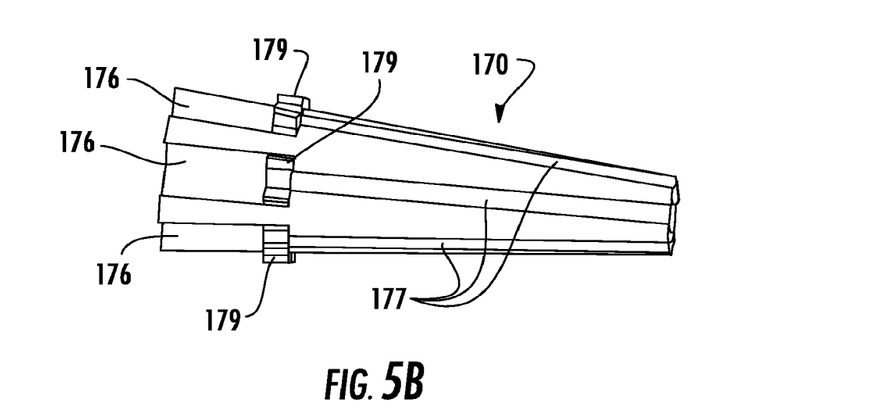

Referring to FIGS. 1 and 2, distal portion 105 can include a plurality of balloons 120*a*-120*e* located on distal portion 105 with bands or rings 122*a*-122*d* provided between adjacent balloons. One or more of rings 122*a*-122*d* may also include a marker that is visible to an imaging system (such as, for example, MRI, x-ray, fluoroscopy and/or ultrasound, not shown) to confirm accurate placement of the balloons 120*a*-120*e* relative to tissue to be treated. In embodiments, each of balloons 120*a*-120*e* can be individually inflated. In embodiments, two or more of balloons 120*a*-120*e* can be simultaneously inflated. In embodiments, a first and third balloon may be inflated while a second balloon positioned between the first and the third balloon remains uninflated. Balloons 120*a*-120*e* may each be the same size or, in embodiments, one or more of balloons 120*a*-120*e* may be of a different size than others of balloons 120*a*-120*e*. Generally, the size of each balloon will be tailored to the size of the tubular structure into which the applicator is being inserted. (FIG. 10) Generally, the balloons may be from 0.1 cm to 10 cm in diameter, in other embodiments from 1 cm to 5 cm in diameter. In embodiments where the applicator is intended for insertion into the esophagus, the balloons may be from 1.5 cm to 3.5 cm in diameter. Balloons 120*a*-120*e* can be fabricated from any biocompatible material capable of inflation. In embodiments, the material from which balloons 120*a*-120*e* are constructed is elastic. The material from which balloons 120*a*-120*e* are constructed may be a single layer or may be a laminate material. Those skilled in the art will readily envision suitable materials for use in making balloons 120*a*-120*e*. While the applicator in the exemplary embodiment of FIG. 1 includes five balloons, it should of course be understood that applicators in accordance with other exemplary embodiments may include three, four, five, six, seven, or even more balloons.

Elongated shaft 115 may include one or more markers 117 that are visible to an imaging system (such as, for example, MRI, x-ray, fluoroscopy and/or ultrasound, not shown) to confirm accurate placement of the applicator relative to tissue to be treated. Elongated shaft 115 may also or instead include one or more numerical indicia 119 to indicate to the clinician the depth to which applicator 100 has been inserted into the tubular structure of the body. Generally, elongated shaft 115 may be from 20 cm to 100 cm in length, in embodiments from 25 cm to 50 cm in length. In embodiments where the applicator is intended for insertion into the esophagus, the elongated shaft may be from 15 cm to 45 cm in length.

In embodiments where each of balloons 120*a*-120*e* are individually inflatable, a series of inflation lumens 126*a*-126*e* are provided. Each inflation lumen 126*a*-126*e* is provided with a stopcock valve 127*a*-127*e* at the proximal end thereof. Inflation lumens 126*a*-126*c* begin adjacent the proximal end with stopcock-capped tubes, the distal ends of which are received within hub 130 such that lumens 126*a*-126*e* extend through hub 130, and continue along the length of flexible elongated shaft 115 to distal portion 105 of applicator 100 where the distal end of each of lumens 126*a*-126*e* opens into one of respective balloons 120*a*-120*e*. Inflation fluid may be any suitable fluid, either a gas or a liquid, and is typically inert. Inflation fluid, where a gas, may be, e.g., air, nitrogen, carbon dioxide or other gas. Inflation fluid, where a liquid, may be water, saline, mineral oil, or other liquid. In embodiments, an inflation fluid may be effective to absorb radiation to, for example, shield, moderate or adjust a dosage of radiation delivered to a patient's tissue from radioactive treatment material contained within source lumen 145.

Guide lumen 150 can be used to slide the applicator 100 over a guide (e.g., cable and/or wire, not shown), for example, from a proximal to a distal location after the guide (not shown) is placed. Alternately or in addition, exemplary applicator 100 can be introduced independently or can be fixed to an endoscope, cable, or guide wire, and can be introduced simultaneously with the endoscope, cable or guide wire placement at the treatment site.

Source lumen 145 can be used to deliver an intended treatment to the site of the tissue to be treated. In embodiments, source lumen 145 is used to deliver radiotherapy, such as, for example brachytherapy, to tissue to be treated. As those skilled in the art will appreciate, there are two defined brachytherapy categories: low dose rate (LDR) brachytherapy and high dose rate (HDR) brachytherapy. The two differ in dose rates of radioisotopes and treatment strategies. Common radioisotopes for LDR brachytherapy include iodine-125 ($^{125}$I) and palladium-103 ($^{103}$Pd), whereas gold-198 ($^{198}$Au) and iridium-192 ($^{192}$Ir) are among the radioisotopes for HDR treatment. Those skilled in the art reading the present disclosure will readily envision other therapies that can be delivered using an applicator in accordance with the present disclosure.

Prior to application of the therapeutic material through source lumen 145, lumen 145 may be used to accommodate a removable stiffening mandrel providing added rigidity during device insertion. Once the applicator is properly positioned, the stiffening mandrel may be removed to allow delivery of the therapeutic material through source lumen 145.

Hub 130 facilitates the connection of the various lumens (126a-126e, 145, 150) with flexible elongated shaft 115. The complexity of the multi lumen catheter design makes injection molding of a suitable hub difficult due to the converging angle of the inflation lumens and the multi-lumen catheter shaft. In the exemplary embodiment illustrated in the drawings, hub 130 includes an outer body 160 and an insert 170 as shown in FIGS. 5A, 5B, 6 and 7. The design of the exemplary embodiment illustrated in the drawings has divided the internal features of the hub, with outer body 160 having the outer portion of the inner features and hub insert 170 having the inner portion of the inner features, the outer body 160 and the hub insert 170 being referred to as a coupling member when the hub insert 170 is inserted into the outer body 160. This advantageously permits injection molding of the components of hub 130 despite the presence of complex internal features. The design of the exemplary embodiment illustrated in the drawings also facilitates the assembly of flexible elongate shaft 115 with the external tubing of the various lumens (126a-126e, 150). The design of the exemplary embodiment illustrated in the drawings also facilitates the alignment of the external tubing of the various lumens (126a-126e, 150) with the channeled features of hub 130.

The outer body 160 of hub 130 includes a distal portion 161 having an opening 164 adapted and configured to receive the proximal end of flexible elongated shaft 115. Glue channels 163 receive glue to secure the proximal end of flexible elongated shaft 115 within opening 164. It should of course be understood that the proximal end of flexible elongated shaft 115 may be secured within opening 164 using other techniques within the purview of one skilled in the art including, but not limited to, ultrasonic welding, friction fit, etc. Outer body 160 of hub 130 includes a proximal portion 162 having channels 166 formed on the inner surface thereof which are adapted and configured to receive the respective distal ends of inflation lumens 126a-126e. Glue channels 168 receive glue to secure the distal ends of inflation lumens 126a-126e within channels 166. It should of course be understood that the distal ends of inflation lumens 126a-126e may be secured within channels 166 using other techniques within the purview of one skilled in the art. Channels 166 step down in size to channels 167 which are adapted and configured to receive coupling tubes 186. The distal ends 169 of channels 167 align with the various lumens in flexible elongated shaft 115. Channel 169 is provided in hub outer body 160 and is adapted and configured to receive the distal end of guide lumen 150.

Hub insert 170 includes channels 176 formed on the inner surface thereof which are adapted and configured to receive respective distal ends of inflation lumens 126a-126e. Channels 176 step down in size to channels 177 which are adapted and configured to receive coupling tubes 186. Channel 178 is provided in hub insert 170 and is adapted and configured to receive the distal ends of guide lumen 150. Hub insert 170 also includes travel stops 179 which seat against the distal end of channels 166 in outer body 160 when the hub insert 170 is assembled with outer body 160.

Figure 7:
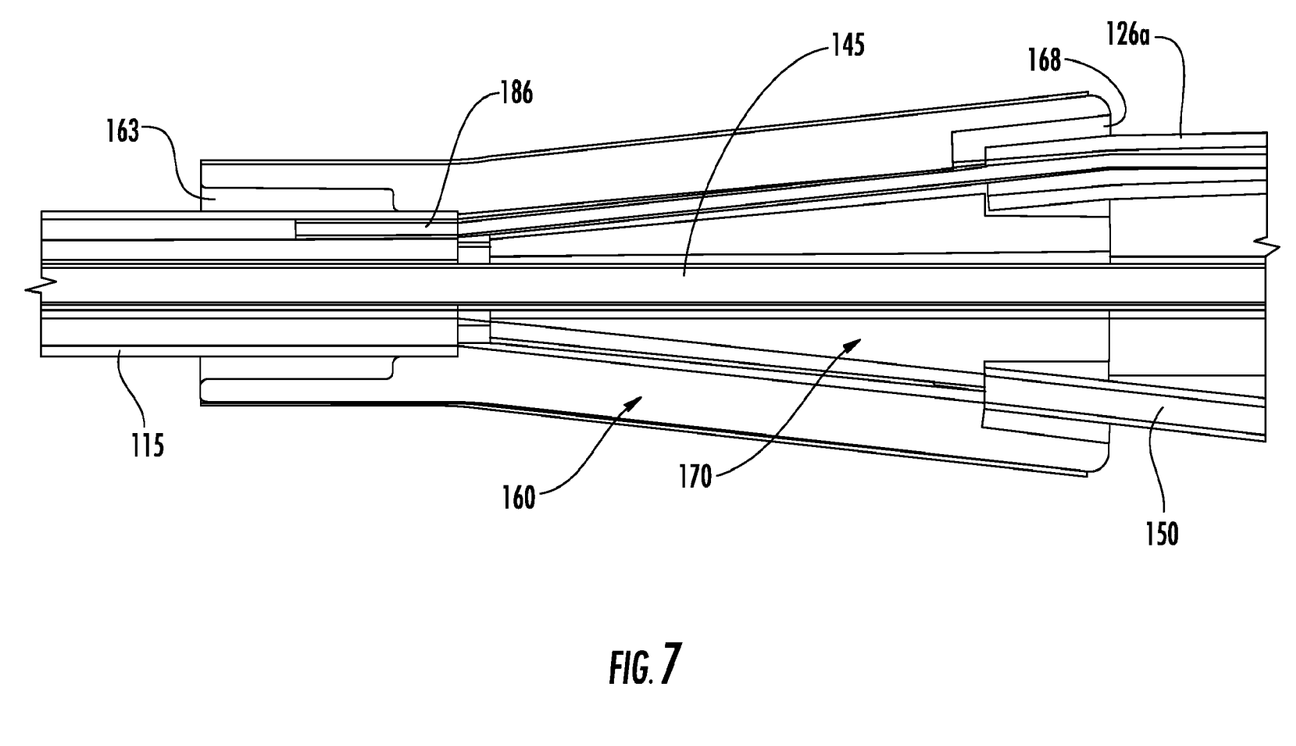
FIG. 7 is a cross-sectional view of the exemplary applicator according to FIG. 1 showing the outer body being assembled with the hub insert with coupling tubes in place coupling the inflation and guide lumens to the flexible elongated shaft.

As those skilled in the art will appreciate, channels 166, 176 cooperate to surround distal ends of inflation lumens 126a-126e which are placed over the proximal ends of coupling tubes 186 when the applicator 100 is assembled. In like manner, channels 167, 177 cooperate to surround distal ends of coupling tubes 186 when the applicator 100 is assembled. Distal ends of coupling tubes 186 are positioned within the corresponding lumen in flexible elongated shaft 115 as shown in FIG. 7.

In an exemplary method of using an applicator in accordance with the present disclosure, a clinician inserts the applicator into the tubular body tissue with all balloons deflated. Once positioned adjacent tissue to be treated using clinical medical imaging technology, one or more of the balloons are inflated with fluid by the clinician by attaching a syringe or other fluid supply to the stopcock valves at the distal end of the inflation lumens corresponding to balloons to be inflated. When the desired number of balloons are inflated to the desired diameter, a therapy source is advanced through the source lumen to deliver therapy to the tissue to be treated. Exemplary applicator 100 can be designed such that any radiation source can be inserted into source lumen 145, including multiple radiations sources at a time. The radiation source can be positioned in source lumen 145 and appropriate balloons inflated such that a radiation dose can be maximally applied to the internal tissue disorder, and yet minimally applied to the surrounding area, thus limiting the patient's healthy tissue to exposure to radiation, and any possible collateral side effects. A radiation source may be positioned within source lumen 145 using suitable techniques, including but not limited to manual or remote afterloading. As those skilled in the art will appreciate, remote afterloading systems provide protection from radiation exposure to healthcare professionals by securing the radiation source in a shielded safe. Once the applicator is correctly positioned in the patient, the applicator is connected to a commercially available 'afterloader' machine (containing the radioactive sources) through source lumen 145. A treatment plan is programmed into the afterloader, which then controls the delivery of the radiation source along the source lumen into the pre-specified position within the applicator. The radiation source remains in place for a pre-specified length of time, again following the treatment plan, following which the radiation source is returned along the source lumen to the afterloader. On completion of delivery of the radioactive source, the applicator is carefully removed from the body.

Figure 8:
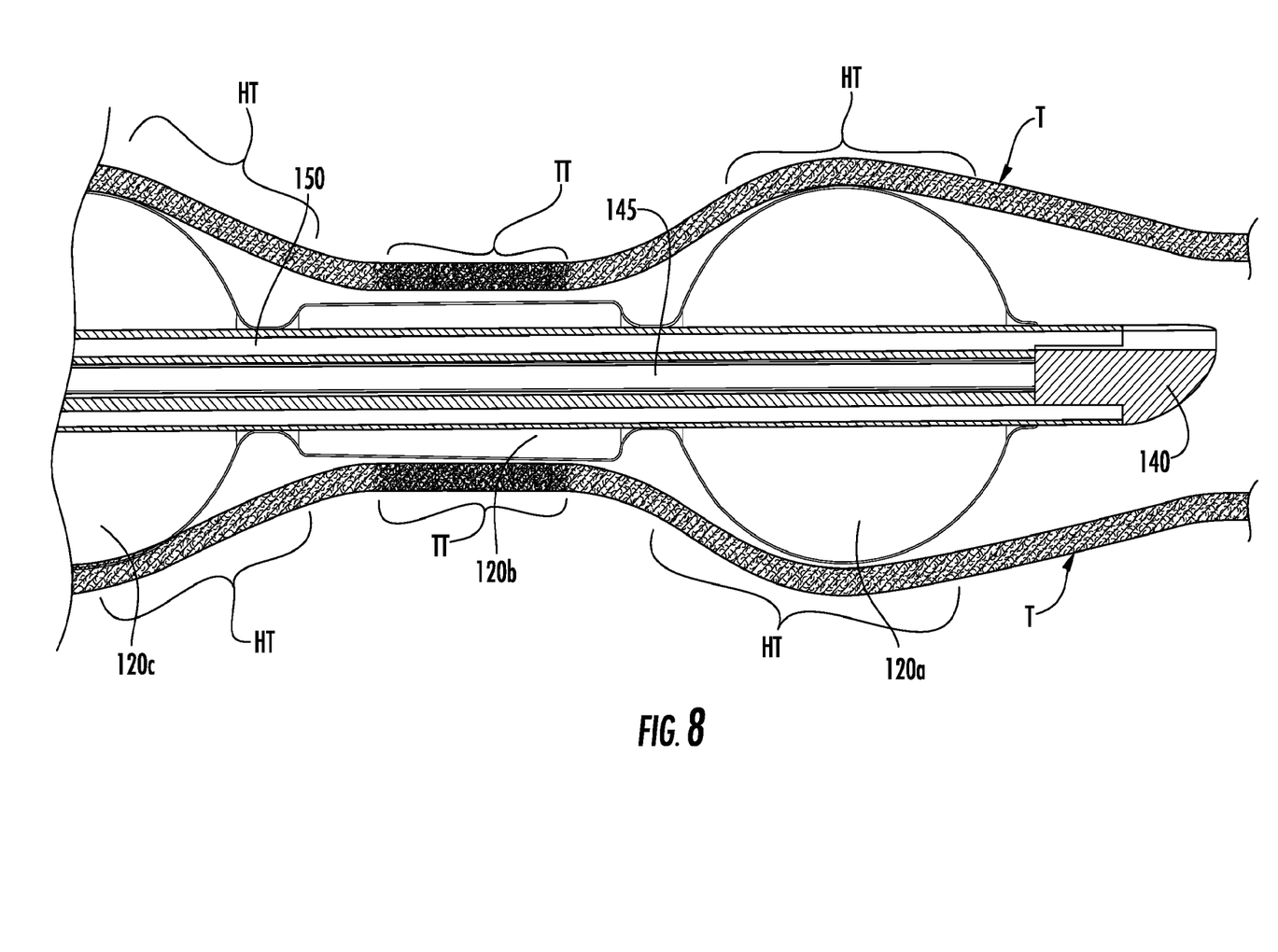
FIG. 8 is an enlarged side cross-sectional view of the exemplary applicator according to FIG. 1 positioned within tubular body tissue.

In the exemplary method illustrated in FIG. 8, after applicator 100 is inserted to the desired position within tubular body tissue "T", distalmost balloon 120a is inflated, balloon 120b immediately proximal of balloon 120a remains uninflated, and the next proximal balloon 120c is inflated. In this manner, target tissue to be treated (e.g., tumor tissue "TT") is approximated more closely to the radiation source present in source lumen 145 at the center of applicator 100 by virtue of the fact that balloon 120b is uninflated, while adjacent healthy tissue ("HT" in FIG. 6) remains further from the radiation source. In this manner, applicators in accordance with the present disclosure provide for improved radiation dose conformity compared to previously known applicators. It should be understood that balloons 120a and 120c can be individually inflated or may be connected to the same inflation lumen so that both balloons 120a, 120c are simultaneously inflated. It should also be understood that the ability to achieve individual inflation provides the clinician with maximum flexibility with respect to exposing only the intended target tissue to the therapeutic levels of radiotherapy while reducing collateral exposure of healthy tissue to radiation. It should also be understood that any combination of balloons may be inflated and remain uninflated. For example, balloon 120a and 120e may be inflated while balloons 120b-102d all remain uninflated. Alternatively, balloons 120a, 102b and 120e may be inflated while balloons 120c and 102d remain uninflated. In other embodiments of the present methods, balloons 120a, 102d and 120e may be inflated while balloons 120b and 102c remain uninflated. Alternatively, balloons 120a and 120c may be inflated while balloons 120b and 102d and 102e remain uninflated. Other combinations of inflation/uninflation will be apparent to those skilled in the art reading this disclosure.

Figure 9:
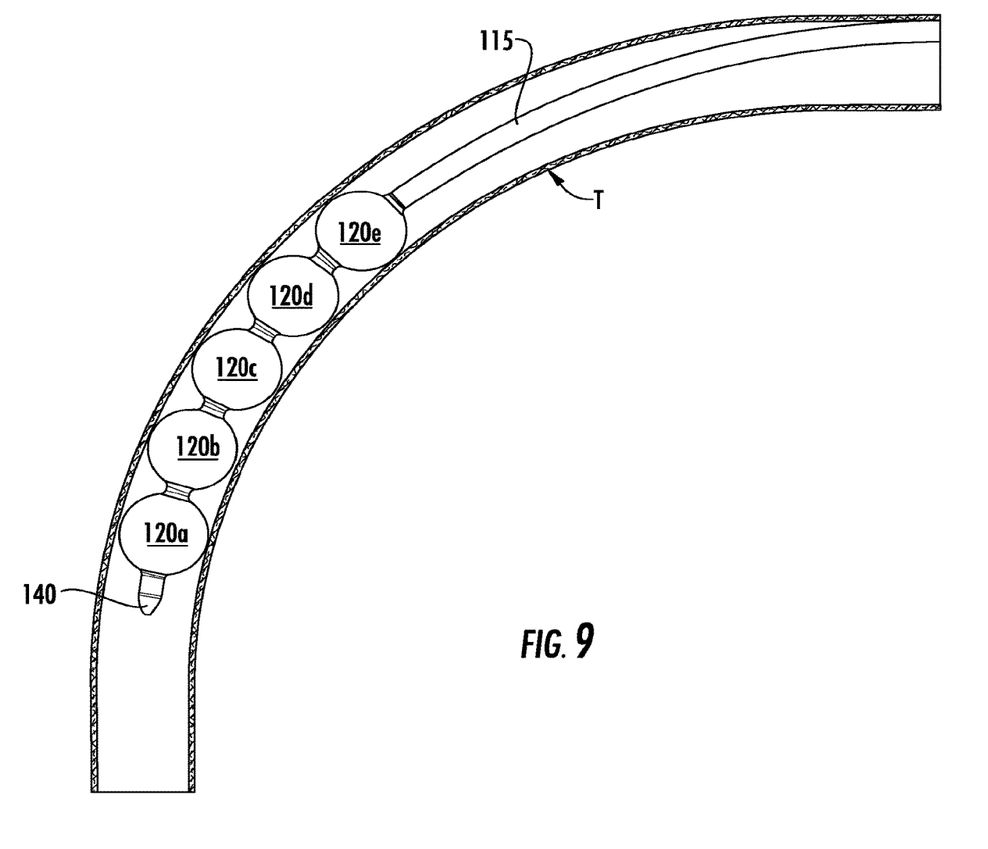
FIG. 9 is a side view of the exemplary applicator according to FIG. 1 positioned within tubular body tissue with all balloons inflated.

Typical catheters will have contact points on a curved anatomy at the outer wall of the lead into to the curve and at the apex of the curve. These contact points would not allow uniform circumferential application of the radiation dose. The presently described applicator having multiple individually inflatable balloons in close proximity enables the source lumen to be centered in the curved anatomy as shown in FIG. 9. The ability to inflate the balloons individually allows the application of relatively equal force to the curved anatomy thereby centering the source lumen and resulting in a more uniform circumferential exposure. As those skilled in the art will appreciate, if the balloons were to be inflated simultaneously the pressure of one balloon in the curve would force the outer balloons to inflate first and to larger diameter than the balloon in the apex.

Figure 10:
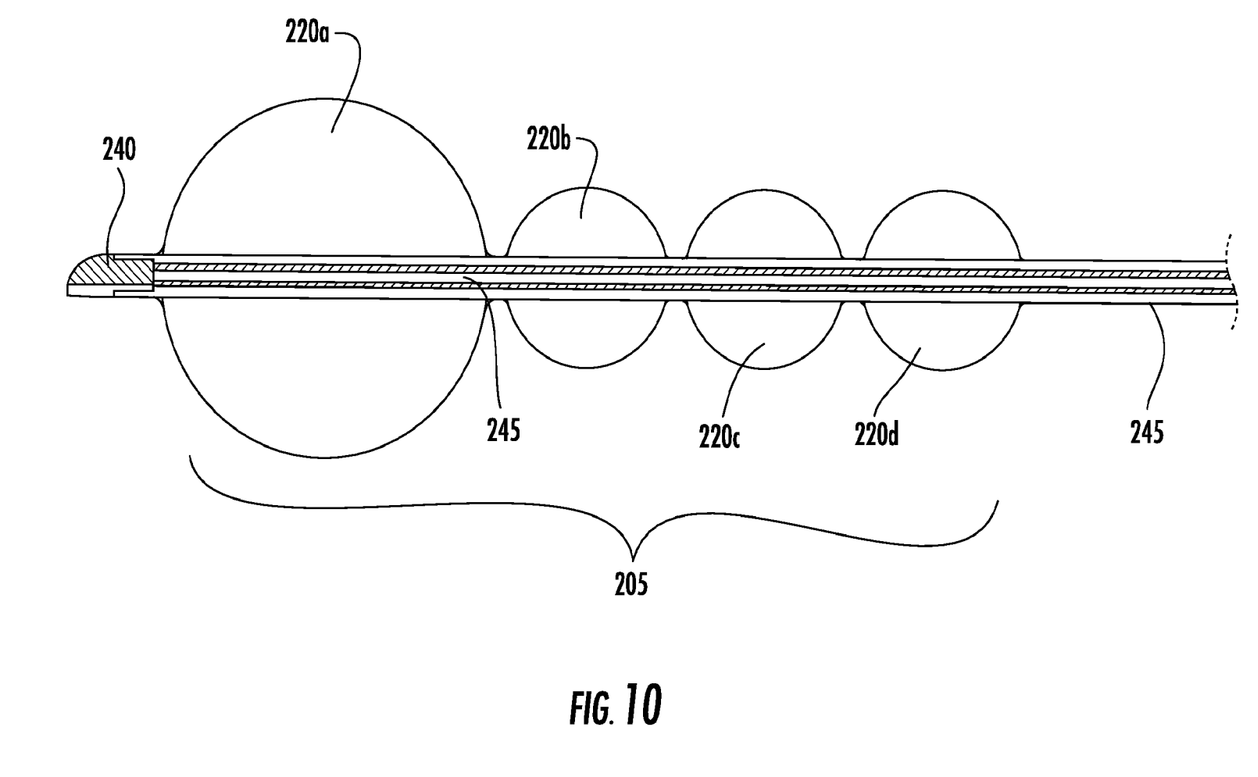
FIG. 10 is a cross-sectional view through the distal end of another exemplary applicator according to the present disclosure.

FIG. 10 shows a cross-sectional view of an applicator 100 according to an exemplary embodiment of the present disclosure in an inflated form, for delivering treatment to an internal tissue disorder. Exemplary applicator 200 has a distal or treatment portion 205 that can be inserted into the tubular structure and a flexible elongated shaft 215. Exemplary applicator 200 also includes a proximal portion (not shown), and a hub (not shown) that are similar in structure and function to those described in connection with the exemplary embodiment of FIG. 1. Source lumen 245 extends through the center of applicator 200 to distal portion 205.

The exemplary embodiment shown in FIG. 10 includes four balloons, 220a-202d, with distalmost balloon 220a being larger that balloons 220b-220d. Distalmost balloon 220a can also serve to anchor the applicator within the tubular body structure, with balloons 220b-220d functioning as shown by balloons 120a-120c in FIG. 6.

Figure 6:
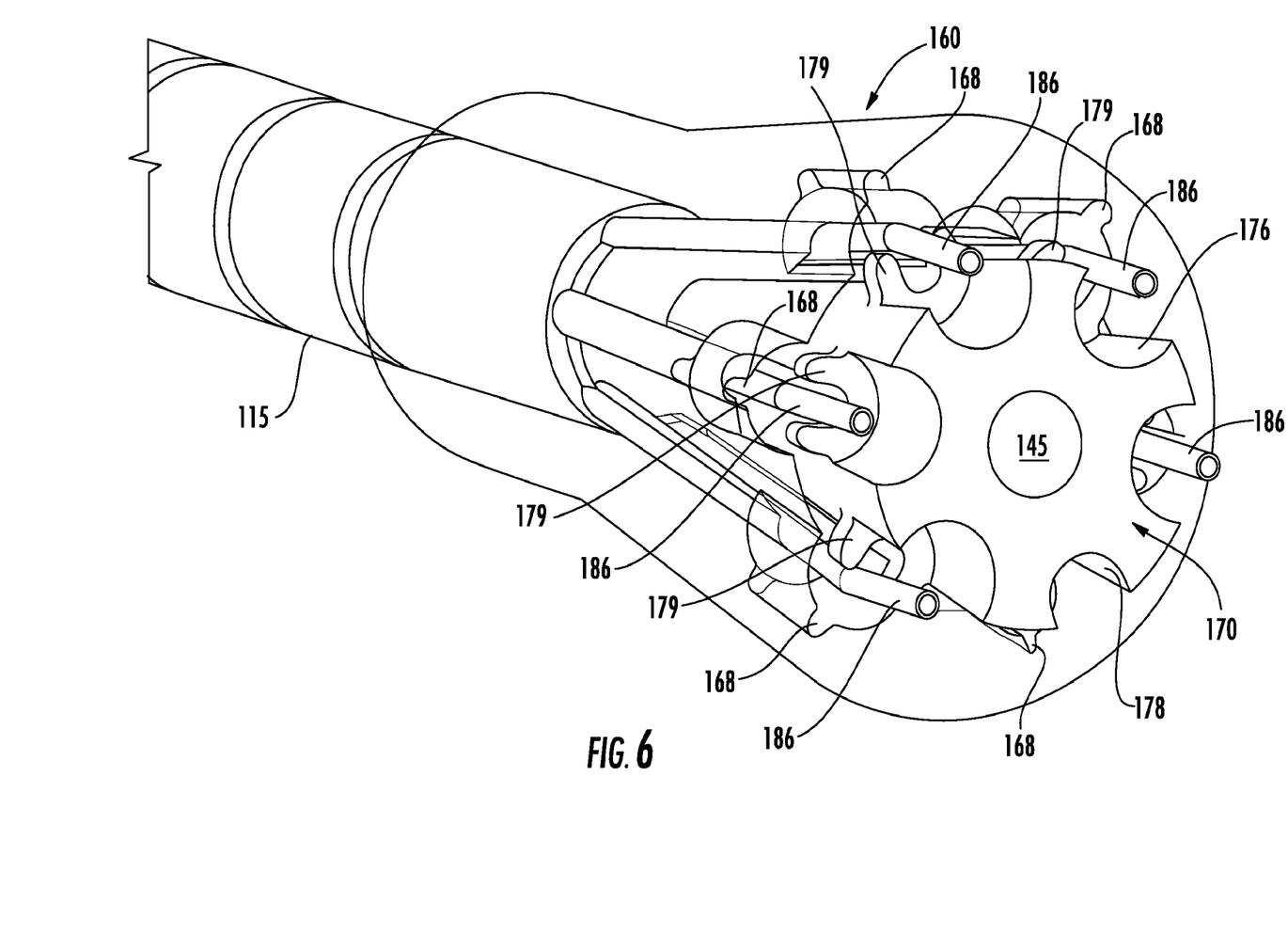
FIG. 6 is a perspective view of the hub of the exemplary applicator according to FIG. 1 with the outer body being formed from a transparent material, the hub insert partially inserted into the outer body, and the proximal end of the flexible elongated shaft inserted into the distal opening of the outer body.

The various components of the applicators described herein can be made of any sterilizable material. In embodiments, all components of the applicators described herein are made of MRI compatible materials. It is further contemplated that some or all of the components can be made of transparent materials, (such as is shown in FIG. 6 with respect to outer body 160 of hub 130) to allow visual confirmation of fluids passing through the various lumens.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:
1. An apparatus for providing radiation treatment to an anatomical lumen comprising muscular tissue, comprising:
an elongated member having the general configuration of a tube formed by a tubular sidewall and having a girth, a proximal end and a distal end, said elongated member defining an internal shaft surrounded by said tubular sidewall, and said elongated member comprising a proximal portion adjacent said proximal end and a distal portion adjacent said distal end;
at least one distal balloon inflation lumen, said at least one distal balloon inflation lumen defined within said tubular sidewall of said elongated member;
at least one proximal balloon inflation lumen, said at least one proximal balloon inflation lumen being positioned within said tubular sidewall of said elongated member;
at least one distal balloon mounted on said distal portion of said elongated member, said at least one distal balloon being inflatable to a size which fills a substantial portion of said anatomical lumen comprising muscular tissue, said at least one distal balloon being inflatable to a girth larger than the girth of said elongated member, said at least one distal balloon being positioned to be placed proximate healthy tissue portions of said anatomical lumen, said at least one distal balloon being in fluidic communication with said at least one distal balloon inflation lumen;
at least one valved distal balloon inflation coupling tube;

at least one proximal balloon mounted on said proximal portion of said elongated member, said at least one distal balloon being positioned between said at least one proximal balloon and said distal end of said elongated member, said at least one proximal balloon being inflatable to a size which fills a substantial portion of said anatomical lumen comprising muscular tissue, said at least one proximal balloon being inflatable to a girth larger than the girth of said elongated member, said at least one proximal balloon being positioned to be placed proximate other healthy tissue portions of said anatomical lumen, said at least one proximal balloon being in fluidic communication with said at least one proximal balloon inflation lumen;

at least one valved proximal balloon inflation coupling tube;

an intermediate region positioned between said at least one distal balloon and said at least one proximal balloon, said intermediate region being positioned to be placed proximate tumorous tissue portions of said anatomical lumen, wherein the anatomical lumen is selected from the group consisting of the esophagus, the rectum, the large intestine, the cardia and the small intestine; and a source lumen adapted and configured to receive a radiation source, the source lumen positioned within said intermediate region;

wherein the intermediate region has a girth smaller than the girth to which said at least one proximal balloon and said at least one distal balloons may be inflated, whereby the girths of said at least one proximal balloon, the intermediate region and said at least one distal balloon cause the anatomical lumen to take a shape where healthy tissue is further displaced from the source lumen as compared to the displacement with respect to the source lumen of tumorous tissue adjacent the intermediate region of the elongated member, and tumorous tissue is positioned closer to said source lumen;

an input coupling member formed separately from and secured to said elongated member for coupling fluidic pressure to said at least one proximal balloon inflation lumen and said at least one distal balloon inflation lumens, said input coupling member defining coupler inputs for receiving at least one respective valved distal balloon inflation coupling tube and respective coupler outputs for coupling to at least one respective balloon inflation lumen, each coupler input and its respective coupler output being positioned at the input and the output of a respective coupler lumen defined in said input coupling member, said coupler lumens each having a non-straight configuration; and wherein said input coupling member comprises:
(i) a hub insert; and
(ii) a hub outer body, said hub insert being positioned within said hub outer body.

2. An apparatus for providing radiation treatment to an anatomical lumen, comprising:
(a) a flexible elongated member having a length and a girth, said flexible elongated member extending between a proximal input and a distal tip, said flexible elongated member comprising a proximal portion adjacent said proximal input and a distal portion adjacent said distal tip, said flexible elongated member defining:
   (i) at least one proximal balloon inflation lumen having an open distal end;
   (ii) at least one distal balloon inflation lumen having an open distal end; and
   (iii) a source lumen having a length, said source lumen being configured and dimensioned to enable delivery of a radiation source to a desired position along the length of the source lumen;
(b) at least one proximal balloon mounted on said proximal portion of said flexible elongated member, said at least one proximal balloon being inflatable to a size which fills a substantial portion of said anatomical lumen, said at least one proximal balloon being inflatable to a girth larger than the girth of said elongated member, one of said at least one proximal balloon lumens opening into one of said at least one proximal balloons;
(c) at least one distal balloon mounted on said distal portion of said flexible elongated member, said at least one distal balloon being positioned between one of said at least one proximal balloons and said distal tip of said flexible elongated member, said at least one distal balloon being inflatable to a size which fills a substantial portion of said anatomical lumen, said at least one distal balloon being inflatable to a girth larger than the girth of said flexible elongated member, one of said at least one distal balloon lumens opening into one of said at least one distal balloons;
(d) a coupling member adapted to be coupled to an inflation fluid source,
wherein said coupling member comprises:
   (i) a hub insert; and
   (ii) a hub outer body, said hub insert being positioned within said hub outer body;
wherein said at least one proximal balloon lumen extends from said proximal input of said flexible elongated member to said distal tip of said flexible elongated member; and
said at least one distal balloon lumen extends from said proximal input of said flexible elongated member to said distal tip of said flexible elongated member; and
(e) a tip member, separately formed from said flexible elongated member, said tip member being adapted to be secured to the distal end of said flexible elongated member, said tip member being positioned and configured to close said open distal end of said proximal balloon inflation lumen and the open distal end of said distal balloon inflation lumen.

3. An apparatus for providing radiation treatment to an anatomical lumen as in claim 2, wherein said source lumen extends from said proximal input of said flexible elongated member to said distal tip of said flexible elongated member.

4. The apparatus of claim 2, further comprising a radiation seed positionable within said source lumen, wherein the source lumen extends substantially along the length of the flexible elongated member radially inwardly with respect to said at least one proximal and said at least one distal balloon lumens.

5. The apparatus of claim 2, wherein the flexible elongated member takes the configuration of a tubular side-wall surrounding a space for containing the source lumen, and wherein a guidewire lumen is defined within said sidewall, said guidewire lumen extending from said proximal input of said elongated member to said distal tip of said elongated member, and said at least one proximal and said at least one distal balloon lumens being defined within said sidewall.

6. The apparatus of claim 5, wherein said at least one proximal balloon lumen, said at least one distal balloon lumen, the source lumen, and the guidewire lumen each have a respective diameter, said guidewire lumen diameter being larger than the proximal balloon lumen diameter and larger than the distal balloon lumen diameter.

7. An apparatus for providing radiation treatment to an anatomical lumen as in claim 2, further comprising said at least one intermediate balloon lumen, one of at least one intermediate balloons mounted and positioned between one of said at least one proximal balloons and one of said at least one distal balloons on said distal flexible elongated member portion, said at least one intermediate balloons being inflatable to a size which fills a substantial portion of said anatomical lumen, said at least one intermediate balloons being inflatable to a girth larger than the girth of said elongated member, one of said at least one intermediate balloon lumens opening into one of said at least one intermediate balloons, wherein all of said at least one intermediate balloon lumens are coupled to said coupling member, said at least one proximal balloon being positioned to be placed proximate healthy tissue portions of said anatomical lumen and said at least one distal balloon being positioned to be placed proximate other healthy tissue portions of said anatomical lumen; whereby the girths of said at least one proximate balloon, said at least one intermediate balloon and said at least one distal balloon cause the anatomical lumen to take a shape where healthy tissue is further displaced from the longitudinal axis of the source lumen as compared to the displacement with respect to the source lumen of tumorous tissue adjacent the intermediate balloon of the elongated member and whereby tumorous tissue is positioned closer to said source lumen and the radiation source contained within the source lumen.

8. An apparatus for providing radiation treatment to an anatomical lumen as in claim 2, wherein an intermediate region is defined along the length of said elongated member between one of said at least one proximal balloon and one of said at least one distal balloon.

9. The apparatus of claim 2 wherein the distal end of said source lumen is closed.

10. The apparatus of claim 2, further comprising a stiffener wherein the stiffener decreases the flexibility of the flexible elongated member.

11. The apparatus of claim 2, wherein said coupling member comprising at least one proximal balloon inflation valve for providing fluid under independently controllable pressure to one of said at least one proximal balloon lumens at said proximal input of said flexible elongated member, and at least one distal balloon inflation valve for providing fluid under independently controllable pressure to one of said at least one distal balloon lumens at said proximal input of said flexible elongated member, whereby one of said at least one proximal balloon and one of said at least one distal balloon may be independently inflated.

12. The apparatus of claim 2, wherein said coupling member is a separate coupling member adapted to be coupled to an inflation fluid source, said coupling member being separately formed from said flexible elongated member.

13. An apparatus for providing radiation treatment to an anatomical lumen, comprising:
(a) a flexible elongated member having a length and a girth, said flexible elongated member extending between a proximal input and a distal tip, said flexible elongated member comprising a proximal portion adjacent said proximal input and a distal portion adjacent said distal tip, said flexible elongated member defining:
(i) at least one proximal balloon inflation lumen having a closed distal end;
(ii) at least one distal balloon inflation lumen having a closed distal end; and
(iii) a source lumen having a length, said source lumen being configured and dimensioned to enable delivery of a radiation source to a desired position along the length of the source lumen;
(b) at least one proximal balloon mounted on said proximal portion of said flexible elongated member, said at least one proximal balloon being inflatable to a size which fills a substantial portion of said anatomical lumen, said at least one proximal balloon being inflatable to a girth larger than the girth of said elongated member, one of said at least one proximal balloon lumens opening into one of said at least one proximal balloons;
(c) at least one distal balloon mounted on said distal of said flexible elongated member, one of said at least one distal balloons being positioned between one of said at least one proximal balloons and said distal tip of said flexible elongated member, said at least one distal balloon being inflatable to a size which fills a substantial portion of said anatomical lumen, said at least one distal balloon being inflatable to a girth larger than the girth of said flexible elongated member, one of said at least one distal balloon lumens opening into one of said said at least one distal balloons; and
(d) a separate coupling member adapted to be coupled to an inflation fluid source, coupling member being separately formed from said flexible elongated member,
wherein said coupling member defines at least one proximal lumen channel feature and at least one distal lumen channel feature for coupling the output of said inflation fluid source to said at least one proximal balloon lumens and said at least one distal balloon lumens, wherein said coupling member comprises:
(i) a hub insert defining an inner portion of said at least one proximal and said at least one distal lumen channel features;
(ii) a hub outer body defining the outer portion of said at least one proximal lumen channel feature and said at least one distal lumen channel feature, said hub insert being positioned within said hub outer body; and
wherein said hub insert and said hub outer body together define a hub member having an output, and said flexible elongated member is mounted in the output of said hub member.

14. An apparatus for providing radiation treatment to an anatomical lumen as in claim 13, wherein said coupling member comprises at least one proximal inflation tube and at least one distal inflation tube, said at least one proximal and said at least one distal inflation tubes each incorporating a respective valve, said at least one proximal inflation tube being mounted in said proximal lumen channel feature, and said at least one distal inflation tube being mounted in said distal lumen channel feature; and further comprising at least one proximal coupling tube having two ends, one of said at least one proximal coupling tube being sealingly engaged at one end with one of said at least one proximal inflation tubes and sealingly engaged at its other end with one of said at least one proximal balloon lumens, and at least one distal coupling tube having two ends, one of said at least one distal coupling tubes being sealingly engaged at one end with one of said at least one distal inflation tubes and sealingly engaged at its other end with one of said at least one distal balloon lumens.

15. An apparatus for providing radiation treatment to an anatomical lumen as in claim 14, wherein said at least one proximal inflation tube is secured by an adhesive in said proximal lumen channel feature, and said at least one distal inflation tube is secured by an adhesive in said distal lumen channel feature.

16. An apparatus for providing radiation treatment to an anatomical lumen as in claim 14, wherein said respective coupling tube at one end is positioned within said at least one inflation tube and secured in place by an adhesive, and said respective coupling tube at its other end is positioned within said at least one balloon lumen and secured in place by an adhesive.

17. An apparatus for providing radiation treatment to an anatomical lumen as in claim 14, further comprising at least one intermediate balloon lumen, at least one intermediate balloon mounted on said distal portion and positioned between said at least one proximal balloon and said at least one distal balloon, said at least one intermediate balloon being inflatable to a size which fills a substantial portion of said anatomical lumen, said at least one intermediate balloon being inflatable to a girth larger than the girth of said elongated member, one of said at least one intermediate balloon lumens opening into one of said at least one intermediate balloons, wherein said at least one intermediate balloon lumen is coupled to said coupling member.

18. The apparatus of claim 13, wherein said coupling member is separately formed from said flexible elongated member.

19. An apparatus for providing radiation treatment to an anatomical lumen, comprising:
(a) an elongated member having a length and a girth, said elongated member extending between a proximal input and a distal tip, said elongated member comprising a proximal portion adjacent said proximal input and a distal portion adjacent said distal tip, said elongated member defining:
(i) at least one proximal balloon lumen having a proximal input and an open distal end;
(ii) at least one distal balloon lumen having a proximal input and an open distal end; and
(iii) a source lumen having a length, said source lumen being configured and dimensioned to enable delivery of a radiation source to a desired position along the length of the source lumen;
(b) at least one proximal balloon mounted on said proximal portion of said elongated member, said at least one one proximal balloon being inflatable to a size which fills a substantial portion of said anatomical lumen, said at least one proximal balloon being inflatable to a girth larger than the girth of said elongated member, one of said at least one proximal balloon lumens opening into one of said at least one proximal balloons;
(c) at least one distal balloon mounted on said distal of said elongated member, said at least one distal balloon being positioned between one of said at least one proximal balloons and said distal tip of said elongated member, said at least one distal balloon being inflatable to a size which fills a substantial portion of said anatomical lumen, said at least one distal balloon being inflatable to a girth larger than the girth of said elongated member, one of said at least one distal balloon lumens opening into one of said at least one distal balloons; and
(d) a coupling member separate from said elongated member adapted to be coupled to an inflation fluid source, said coupling member comprising at least one proximal balloon inflation valve for providing fluid under independently controllable pressure to one of said at least one proximal balloon lumens at said proximal input of said elongated member, and at least one distal balloon inflation valve for providing fluid under independently controllable pressure to one of said at least one distal balloon lumen at said proximal input of said elongated member, whereby said at least one proximal balloon and said at least one distal balloon may be independently inflated;
wherein said at least one proximal balloon lumen extends from said proximal input of said elongated member to said distal tip of said elongated member; and
said at least one distal balloon lumen extends from said proximal input of said elongated member to said distal tip of said elongated member
wherein said coupling member is coupled to said proximal input of said elongated member,
said coupling member defining coupling member passages, said coupling member passages being coupled in sealing relationship to a respective one of said proximal inputs of said proximal balloon lumen and said distal balloon lumen; and
(e) a tip member, separately formed from said elongated member, said tip member being adapted to be secured to the distal end of said elongated member, said tip member being positioned and configured to close said open distal end of said proximal balloon inflation lumen and the open distal end of said distal balloon inflation lumen.

20. The apparatus of claim 19, wherein said coupling member is separate from said elongated member.

* * * * *